US008751010B2

(12) United States Patent
Rondoni et al.

(10) Patent No.: US 8,751,010 B2
(45) Date of Patent: Jun. 10, 2014

(54) TIME TO NEXT RECHARGE SESSION FEEDBACK WHILE RECHARGING AN IMPLANTABLE MEDICAL DEVICE, SYSTEM AND METHOD THEREFORE

(75) Inventors: John C. Rondoni, Plymouth, MN (US); Jon P. Davis, St. Michael, MN (US); Kevin L. Bright, Maple Grove, MN (US); Rajeev M. Sahasrabudhe, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1745 days.

(21) Appl. No.: 12/112,719

(22) Filed: Apr. 30, 2008

(65) Prior Publication Data

US 2009/0276015 A1 Nov. 5, 2009

(51) Int. Cl.
*A61N 1/00* (2006.01)

(52) U.S. Cl.
USPC .............................. 607/61; 607/33

(58) Field of Classification Search
USPC ............ 607/33, 61, 32, 60; 320/132, DIG. 21
See application file for complete search history.

(56) References Cited

U.S. PATENT DOCUMENTS

| 4,949,046 A | | 8/1990 | Seyfang |
| 4,952,862 A | | 8/1990 | Biagetti et al. |
| 5,185,566 A | | 2/1993 | Goedken et al. |
| 5,349,540 A | | 9/1994 | Birkle et al. |
| 5,411,537 A | | 5/1995 | Munshi et al. |
| 5,565,759 A | * | 10/1996 | Dunstan ........................ 320/135 |
| 5,656,919 A | * | 8/1997 | Proctor et al. ................. 320/153 |
| 5,690,685 A | | 11/1997 | Kroll et al. |
| 5,723,971 A | | 3/1998 | Sakai et al. |
| 5,789,900 A | | 8/1998 | Hasegawa et al. |
| 5,926,007 A | * | 7/1999 | Okada ........................... 320/132 |
| 5,982,147 A | * | 11/1999 | Anderson ..................... 320/132 |
| 6,169,387 B1 | | 1/2001 | Kaib |
| 6,198,253 B1 | | 3/2001 | Kurle et al. |
| 6,278,258 B1 | | 8/2001 | Echarri et al. |
| 6,329,793 B1 | | 12/2001 | Bertness et al. |
| 6,516,227 B1 | * | 2/2003 | Meadows et al. ............... 607/46 |
| 6,553,263 B1 | | 4/2003 | Meadows et al. |
| 6,842,460 B1 | | 1/2005 | Olkkonen et al. |
| 6,892,148 B2 | | 5/2005 | Barsoukov et al. |
| 6,928,372 B2 | * | 8/2005 | Pozsgay et al. ................. 702/63 |
| 6,940,255 B2 | * | 9/2005 | Loch ............................ 320/132 |

(Continued)

FOREIGN PATENT DOCUMENTS

| EP | 1 048 324 A2 | 11/2000 |
| EP | 1 610 437 A1 | 12/2005 |

(Continued)

OTHER PUBLICATIONS

International Search Report for PCT/US2009/031624.

*Primary Examiner* — Mark W Bockelman
(74) *Attorney, Agent, or Firm* — IPLM Group, P.A.

(57) ABSTRACT

A system and method for determining, during a recharge session, an amount of time until a subsequent recharge session is required to charge a rechargeable power source of an implantable medical device. A model allows a determination of the time until recharge without suspending charging during the recharge session by basing the determination on an initial measured battery voltage and a present current into the rechargeable power source. Alternatively, charging is suspended during the recharge session, and voltage measurements are taken, after which time charging is resumed, without patient input or suspending the recharge session.

24 Claims, 9 Drawing Sheets

(56) References Cited

U.S. PATENT DOCUMENTS

| | | |
|---|---|---|
| 7,109,684 B2 | 9/2006 | Takaoka et al. |
| 7,245,107 B2 | 7/2007 | Moore et al. |
| 7,248,929 B2 | 7/2007 | Meadows et al. |
| 7,317,947 B2 | 1/2008 | Wahlstrand et al. |
| 7,865,245 B2 | 1/2011 | Torgerson et al. |
| 7,881,796 B2 | 2/2011 | Scott et al. |
| 8,319,479 B2 * | 11/2012 | Kao et al. ............ 320/157 |
| 2002/0140399 A1 | 10/2002 | Echarri et al. |
| 2003/0085684 A1 | 5/2003 | Tsukamoto et al. |
| 2003/0114899 A1 | 6/2003 | Woods et al. |
| 2004/0017180 A1 | 1/2004 | Cook |
| 2004/0162592 A1 | 8/2004 | Betzold et al. |
| 2004/0220758 A1 | 11/2004 | Barsoukov et al. |
| 2005/0004619 A1 | 1/2005 | Wahlstrand et al. |
| 2005/0075693 A1 | 4/2005 | Toy et al. |
| 2005/0110466 A1 | 5/2005 | Shoji et al. |
| 2005/0277994 A1 | 12/2005 | McNamee et al. |
| 2007/0063683 A1 | 3/2007 | Coq et al. |
| 2007/0069687 A1 | 3/2007 | Suzuki |
| 2007/0090790 A1 | 4/2007 | Hui |
| 2007/0156205 A1 | 7/2007 | Larson et al. |
| 2007/0257636 A1 | 11/2007 | Phillips et al. |
| 2008/0097544 A1 | 4/2008 | Gandhi et al. |
| 2008/0258679 A1 | 10/2008 | Manico et al. |
| 2009/0163820 A1 | 6/2009 | Eerden |

FOREIGN PATENT DOCUMENTS

| | | |
|---|---|---|
| JP | 2006 046919 A | 2/2006 |
| WO | WO01/08749 A1 | 2/2001 |
| WO | WO01/34243 A1 | 5/2001 |
| WO | WO2008/038202 A2 | 4/2008 |

* cited by examiner

TIME TO NEXT RECHARGE SESSION FEEDBACK WHILE RECHARGING AN IMPLANTABLE MEDICAL DEVICE, SYSTEM AND METHOD THEREFORE

FIELD

The present invention relates generally to controllers, systems and methods for implantable medical devices and, more particularly, to such controllers, systems and methods for managing the recharging of rechargeable power sources associated with implantable medical devices.

BACKGROUND

The medical device industry produces a wide variety of electronic devices for treating patient medical conditions. Depending upon the medical condition, medical devices can be surgically implanted or connected externally to the patient receiving treatment. Medical professionals or other clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices designed to deliver therapeutic electrical stimulation include neurological stimulators, pacemakers, defibrillators and drug pumps. Most implantable medical devices are powered by an internal battery or other power source associated with or internal to the device.

Because surgery is required to implant most implantable medical devices, it is desirable, particularly in devices that consume power quickly, to make the internal battery rechargeable. An external power source may then be used to recharge the rechargeable battery, commonly transcutaneously via an inductive link between an external coil and an internal coil. Depending on the nature of the implantable medical device and rechargeable battery in question, several hours will commonly be required to fully recharge the rechargeable battery. While some implantable medical devices may be able to deliver therapy to a patient for months or years on a single charge, some devices, particularly those that deliver a relatively large amount of therapy constantly, may consume all of the charge in a battery in a matter of days or weeks.

Commonly, in order to recharge their implantable medical device, patients may sit in close proximity of their external charger, maintaining a recharging head, or the entire external charging device, nearby or within a few inches of their implantable medical device. The rechargeable battery can commonly require several hours to charge from a relatively low amount of charge to a full or nearly-fully level of charge.

SUMMARY

The need of some patients to spend some time, e.g. several hours, periodically every week charging their implantable medical device, and thus being relatively immobile with a charger held against their implantable medical device, may lead to a number of frustrations on the part of patients. Not the least of these is that, while charging of a rechargeable power source associated with the IMD is proceeding, the patient may not have any way of knowing how long it may take for the charge level of a rechargeable power source associated with an implantable medical device to charge or recharge fully, or mostly fully. Many patients may not like to have to put their lives on hold during recharging, and it may become all the more irritating when they don't know how long the recharging is going to last. At an even more basic level, recharging devices may not ultimately provide any particularly meaningful feedback during recharging of any kind. Thus, patients may not know, for instance, whether they are positioning the external charger in an optimal configuration.

The act of recharging a rechargeable battery may make determinations as to battery charge as a function of voltage unreliable. In an embodiment, the present invention may thus determine the charge in the rechargeable battery as a function of current into the rechargeable battery and the voltage of the battery at the start of the recharging session, applied to a known model of the rechargeable battery. Combined with projections of charge use based on current device settings and past usage, the current anticipated charge duration of the rechargeable battery may be determined and updated regularly throughout a recharge session automatically, without patient actions and without ceasing charging. In an alternative embodiment, the external charging device may momentarily suspend charging in order to obtain the parameter measurements needed to make an accurate determination of the charge in the rechargeable battery without the need for a model. Again, this may require no actions from the patient, and the patient may regularly be supplied with updated estimates of how much charge duration is currently stored in the rechargeable battery.

In an embodiment, the present invention provides a recharge management system, comprising an implantable medical device having a rechargeable power source, an external charger configured to charge the rechargeable power source when placed in proximity to the implantable medical device, electronic componentry, operatively coupled to the implantable medical device, configured to determine the recharge interval should the recharging session not continue; and a user output, operatively coupled to the electronic componentry, configured to communication the recharge interval to a user.

In an embodiment, the electronic componentry determines the recharge interval by applying a model.

In an embodiment, the electronic componentry is further configured to measure an initial power source voltage of the rechargeable power source before the external charger begins to charge the rechargeable power source, and wherein the implantable medical device further comprises a current meter, the current meter configured to measure current to the rechargeable power source, and wherein the model utilizes the initial power source voltage and the measured current to determine the recharge interval.

In an embodiment, the rechargeable power source has a power source voltage, a charge capacity and a charge level, and wherein the electronic componentry is further configured to measure the power source voltage during a time in which the external charging has suspended charging of the rechargeable power source determine the charge level as a function of the power source voltage and the charge capacity; and determine the recharge interval based on the charge level.

In an embodiment, the recharge interval is determined based on a present programmed rate.

In an embodiment, the recharge interval is determined based on a past programmed rate.

In an embodiment, the recharge interval is determined based on a present programmed rate and a past programmed rate.

In an embodiment, the implantable medical device has a programmed therapeutic output having a programmed rate, and wherein the recharge interval is further determined based on the programmed rate.

In an embodiment, the system further comprises a user input, wherein the user inputs via the user input a prospective therapeutic output having a prospective rate, and wherein the recharge interval is determined based on the prospective rate should the recharging session not continue.

In an embodiment, the system further comprises a user input wherein the user inputs a desired time interval, wherein the rechargeable power source further comprises a present charge level, and wherein the electronic componentry further determines an estimated time to charge the rechargeable power source based on the present charge level and the desired time interval.

In an embodiment, the user input is a component of the external charger.

In an embodiment, the electronic componentry is a component of the implantable medical device.

In an embodiment, the electronic componentry is a component of the external charger.

In an embodiment, the user output is a component of the external charger.

In an embodiment, the present invention further provides a method for determining a recharge interval until a recharge time when a charge level of a rechargeable power source of an implantable medical device reaches a value at which recharging of the rechargeable power source is indicated, comprising the steps of charging the rechargeable power source with an external charger during a recharging session, determining, during the recharging session, the recharge interval should the recharging session not continue, and outputting the recharge interval to a user.

In an embodiment, the rechargeable power source has a power source voltage, a charge capacity and a charge level, and wherein the determining step further comprises suspending the charging step, measuring the power source voltage, recommencing the charging step, determining the charge level as a function of the power source voltage and the charge capacity, and determining the recharge interval based on the charge level.

DRAWINGS

DESCRIPTION

In order to maximize the efficiency and effectiveness of recharging sessions of implantable medical devices equipped with rechargeable power sources, it is desirable to provide patients with information relating to the recharging session. Accurate information may help the patient better plan for, and conduct recharging sessions. Patients may want to know how long the charge that is currently stored in their rechargeable power source may last in order, for example, to better plan their schedule to account for recharging which will ultimately be needed. This is especially true during charging of the rechargeable power source. Patients may want to know how long the charge that is currently stored in the rechargeable power source may last if charging ceased at that point even while recharging the power source. For example, a user may want to know whether the charge that has been put into the rechargeable power source at a given point in the charging process is sufficient to allow enough time for the user to accomplish a particular tasks or tasks, such as attend an event or travel to a particular destination. However, methods understood in the art may not allow for accurately determining a charge level in a rechargeable power source while it is being recharged due to the interference of the charging current and voltage.

In an embodiment, a system and method has been developed that may allow for a determination, for example during charging, of the charge level of a rechargeable power source of an implantable medical device and, by extension, the anticipated duration of the battery charge given expected device usage. Rather than measuring the voltage of the rechargeable power source, as is known in the art, the charging current may be measured and combined with a rechargeable power source voltage measured before charging began and applied to a model of the performance of the rechargeable power source in question. The result may be the ability to provide current estimates of the duration of the charge in the rechargeable power source to the patient without having to cease recharging. Alternatively, charging may be temporarily, automatically suspended, at which time a standard measurement is taken and charge duration determined, without having to suspend the recharging session.

Figure 1:
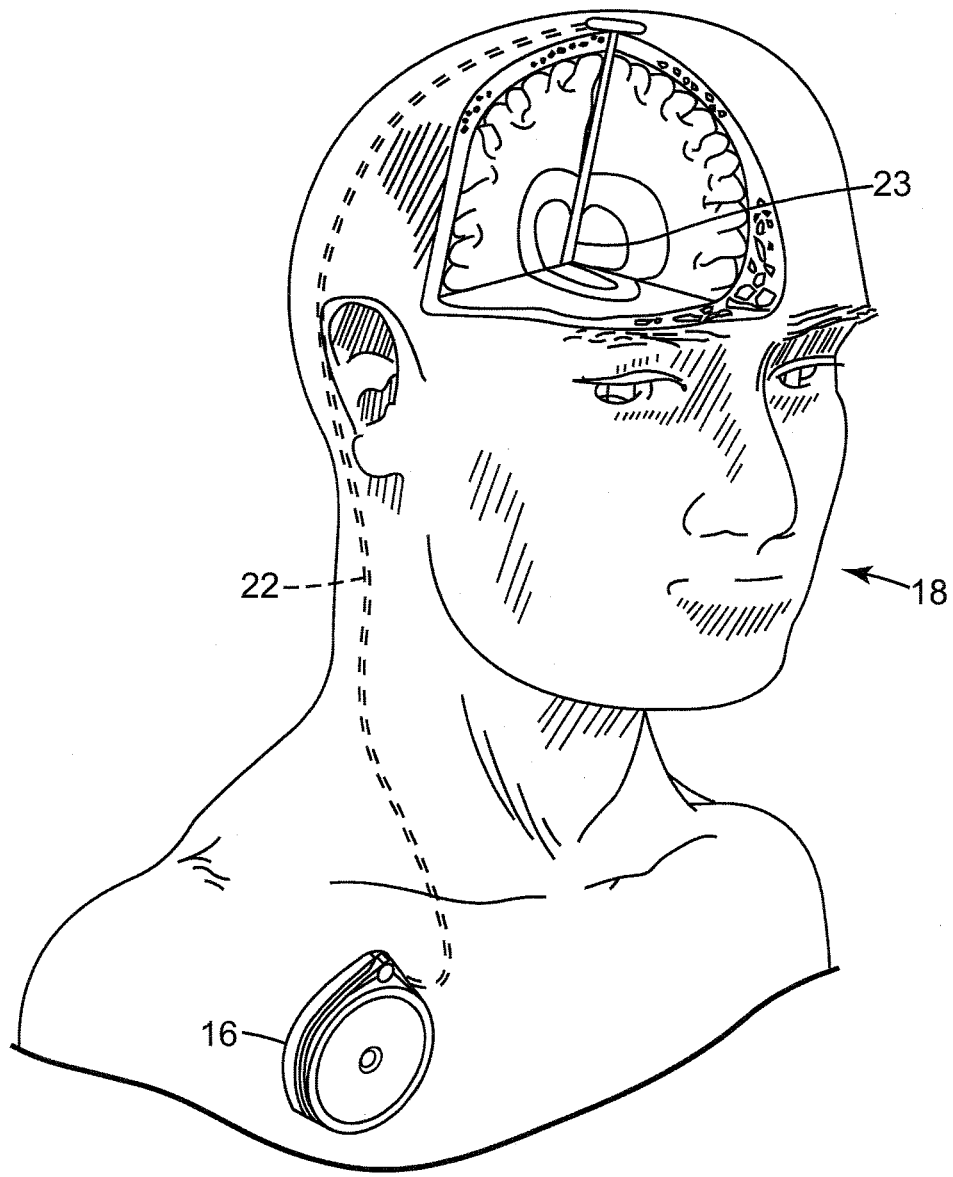
FIG. 1 shows an example of an implantable medical device, e.g. a neurological stimulator, implanted, with electrodes positioned leading into the patient's brain.

Use of an external power source having an antenna with a plurality of concentric primary coils can generally be illustrated by the generic system in FIG. 1, which shows implantable medical device 16, for example, a neurological stimulator, implanted in patient 18. The implantable medical device 16 is typically implanted by a surgeon in a sterile surgical procedure performed under local, regional, or general anesthesia. Before implanting the medical device 16, a lead 22 is typically implanted with the distal end position at a desired therapeutic delivery site 23 and the proximal end tunneled under the skin to the location where the medical device 16 is to be implanted. Implantable medical device 16 is generally implanted subcutaneously at depths, depending upon application and device 16, of from 1 centimeter (0.4 inches) to 2.5 centimeters (1 inch) where there is sufficient tissue to support the implanted system. Once medical device 16 is implanted into the patient 18, the incision can be sutured closed and medical device 16 can begin operation.

Implantable medical device 16 can be any of a number of medical devices such as an implantable therapeutic substance delivery device, implantable drug pump, electrical neurological stimulator, cardiac pacemaker, cardioverter or defibrillator, as examples.

If implantable medical device 16 is a drug infusion device, for example, implantable medical device 16 operates to infuse a therapeutic substance into patient 18, and lead 22 may be substituted for an appropriate piece of equipment, such as a catheter. If implantable medical device 16 is a neurological stimulator, implantable medical device 16 operates to electrically stimulate tissue in patient 18 in order to obtain a physiologic response. Implantable medical device 16 can be used for a wide variety of therapies such as pain, spasticity, cancer, and many other medical conditions.

If implantable medical device 16 is a drug pump, for example, the therapeutic substance contained in implantable medical device 16 may be a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

Figure 2:
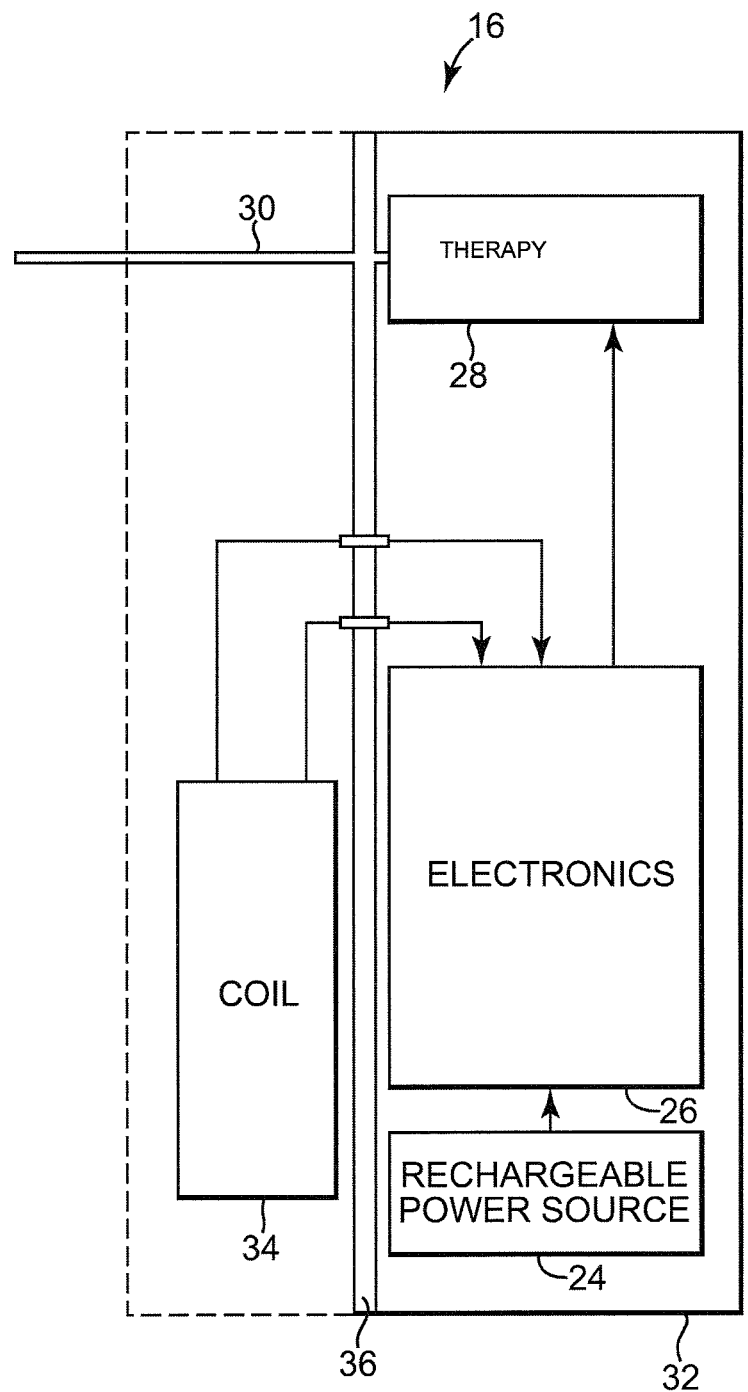
FIG. 2 shows an exemplary block diagram of an implantable neurological stimulator of FIG. 1.

If implantable medical device 16 is an electrical stimulator, for example, a therapy module 28 such as described in reference to FIG. 2 may deliver an electrical stimulus, such as an electrical pulse, or series of electrical pulses, either monopolar or bi-polar, through one or more electrical leads and/or electrodes to provide specific or general benefit to that patient such as pain relief or muscular control.

In FIG. 2, implantable medical device 16 has a rechargeable power source 24, such as a Lithium ion battery, powering electronics 26 and therapy module 28 in a conventional manner. Alternatively, coil 34, rechargeable power source 24, or both, may be located outside of housing 32. Therapy module 28 is coupled to patient 18 through one or more therapy connections 30 which may deliver therapy at a programmed rate, also conventionally. Rechargeable power source 24, electronics 26 and therapy module 28 are contained in hermetically sealed housing 32. Secondary charging coil 34 is attached to the exterior of housing 32. Secondary charging coil 34 is operatively coupled through electronics 26 to rechargeable power source 24. In an alternative embodiment, secondary charging coil 34 could be contained in housing 32 or could be contained in a separate housing umbilically connected to electronics 26. Electronics 26 help provide control of the charging rate of rechargeable power source 24 in a conventional manner. Magnetic shield 36 is positioned between secondary charging coil 34 and housing 32 in order to protect rechargeable power source 24, electronics 26 and therapy module 28 from electromagnetic energy when secondary charging coil 34 is utilized to charge rechargeable power source 24.

Rechargeable power source 24 can be any of a variety power sources including a chemically based battery or a capacitor. Rechargeable power source may be a well known lithium ion battery.

Figure 3:
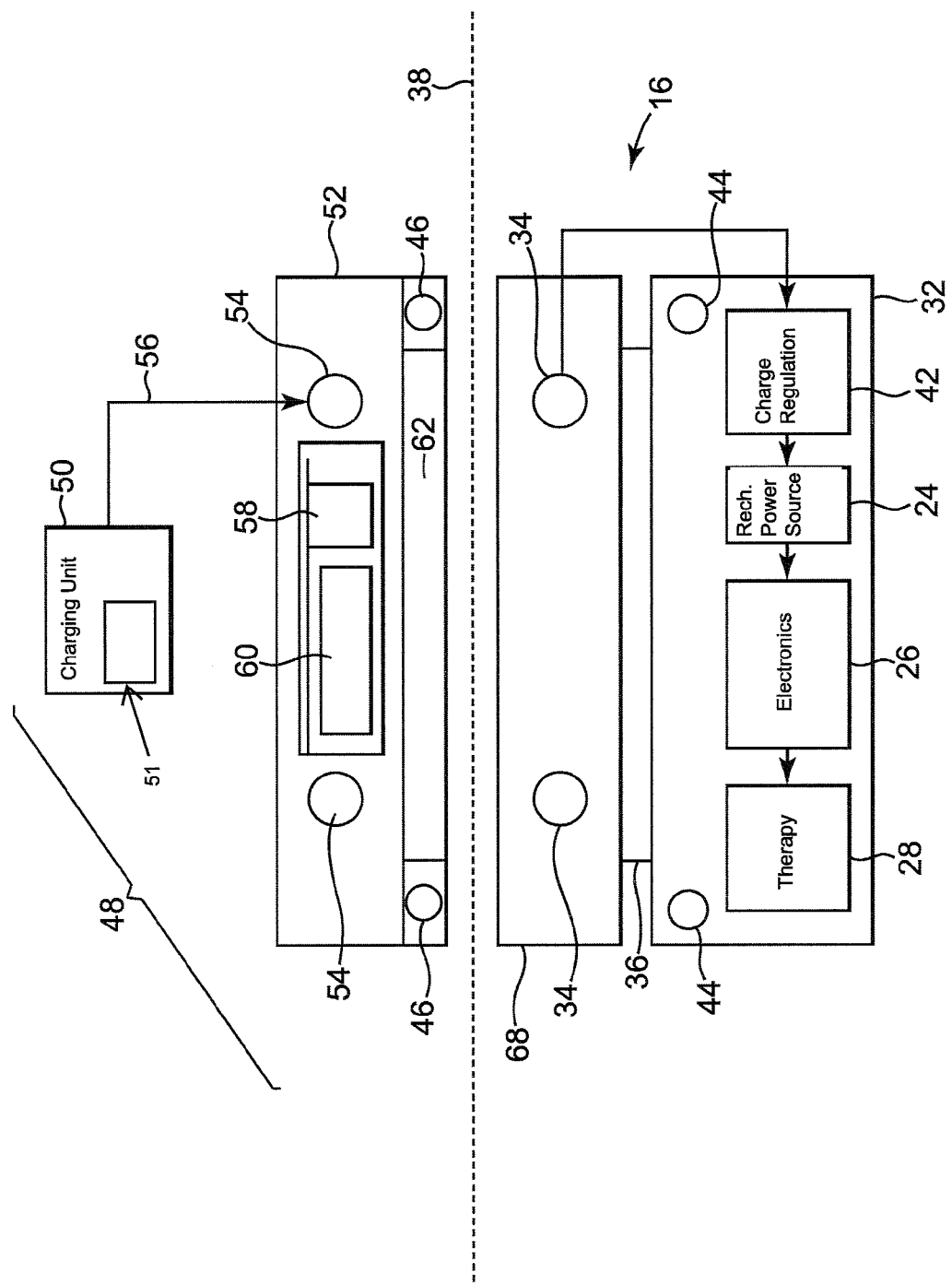
FIG. 3 shows a more descriptive block diagram of the implantable neurological stimulator of FIG. 2 and a block diagram of an external charging device.

FIG. 3 illustrates an alternative embodiment of implantable medical device 16 situated under cutaneous boundary 38. Implantable medical device 16 is similar to the embodiment illustrated in FIG. 2. However, charging regulation module 42 is shown separate from electronics 26 controlling therapy module 28. A current meter or coulomb counter may be included in charging regulation module 42 to measure input current or charge that is delivered to rechargeable power source 24 during a recharge session. In such an embodiment, the current meter or coulomb counter should come after power regulators in charging regulation module 42 in order to accurately reflect the current or charge being delivered to rechargeable power source 24. Again, charging regulation and therapy control is conventional. Implantable medical device 16 also has internal telemetry coil 44 configured in a conventional manner to communicate through external telemetry coil 46 to an external programming device (not shown), charging unit 50 or other device in a conventional manner in order to both program and control implantable medical device 16 and to externally obtain information from implantable medical device 16 once implantable medical device 16 has been implanted. Internal telemetry coil 44 may be rectangular in shape with dimensions of 1.85 inches (4.7 centimeters) by 1.89 inches (4.8 centimeters) constructed from 150 turns of 43 AWG wire and may be sized to be larger than the diameter of secondary charging coil 34 of internal antenna 68. In one embodiment, secondary coil 34 is constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Optionally, magnetic shield 36 is positioned, in one embodiment, between secondary charging coil 34 and housing 32 and sized to cover the footprint of secondary charging coil 34.

Internal telemetry coil 44, having a larger diameter than secondary coil 34, is not completely covered by magnetic shield 36 allowing implantable medical device 16 to communicate with the external programming device with internal telemetry coil 44 in spite of the presence of magnetic shield 36.

Rechargeable power source 24 can be charged while implantable medical device 16 is in place in a patient through the use of external charging device 48. In an embodiment, external charging device 48 consists of charging unit 50 and external antenna 52. Charging unit 50 contains electronics 51 necessary to drive primary coil 54 with an oscillating current in order to induce current in secondary coil 34 when primary coil 54 is placed in the proximity of secondary coil 34. Electronics 51 may also determine an estimated time until recharging is required. In alternative embodiments, electronics 26 may determine the estimated time until recharge is required. In yet another embodiment, neither electronics 51 in external charging device 48 nor electronics 26 in implantable medical device 16 are used, and some other device which may be operatively coupled with either implantable medical device 16 or external charging device 48, or both, is employed instead. Charging unit 50 is operatively coupled to primary coil by cable 56. In an alternative embodiment, charging unit 50 and antenna 52 may be combined into a single unit. Antenna 52 may also optionally contain external telemetry coil 46 which may be operatively coupled to charging unit 50 if it is desired to communicate to or from implantable medical device 16 with external charging device 48. Alternatively, antenna 52 may optionally contain external telemetry coil 46 which can be operatively coupled to an external programming device, either individually or together with external charging unit 48. Alternatively, electronics may be located in or associated with implantable medical device 16, external charging device 48, a patient programmer, or a physician programmer, in various embodiments.

In an embodiment, repositionable magnetic core 58 may help to focus electromagnetic energy from primary coil 54 to more closely be aligned with secondary coil 34. In an embodiment, energy absorptive material 60 can help to absorb heat build-up in external antenna 52 which will also help allow for a lower temperature in implantable medical device 16 and/or help lower recharge times. In a further embodiment, thermally conductive material 62 is positioned covering at least a portion of the surface of external antenna 52 which contacts cutaneous boundary 38 of patient 18.

FIGS. 4-9 depict a series of screenshots from a display in external charging device 48 used for conveying information related to the charging of implantable medical device 16 to a user, such as patient 18. It is recognized that in alternative embodiments, the display could be associated with a physician programmer, a patient programmer, or any other external devices with componentry suitable to communicate with implantable medical device 16 and display the information described below.

Figure 4:
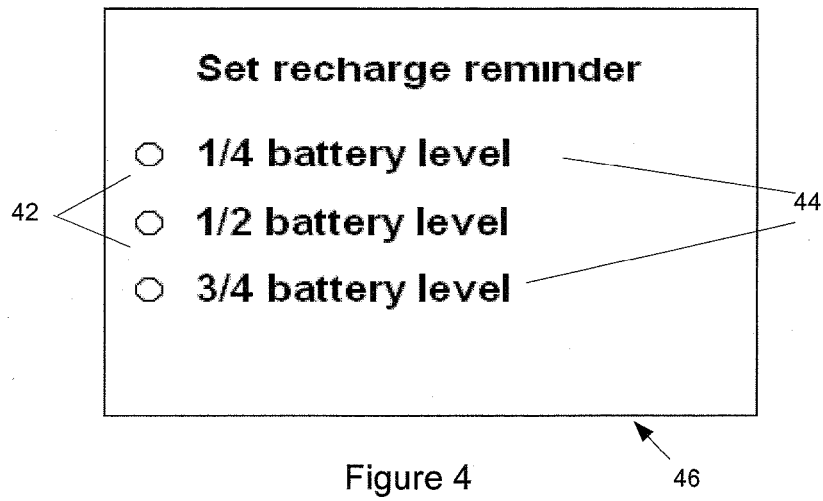
FIG. 4 shows a screen shot of a window for allowing a user to select when to receive a reminder to recharge their implantable medical device.

FIG. 4 shows a screenshot 146 allowing a user to program a reminder to conduct a recharge session when the charge on rechargeable power source 24 falls below a selected point. In an embodiment, the user may use radio buttons 142 to choose one of several percentages 144 of rechargeable power source 24 capacity at which the reminder should be given. Which percentage 144 that may be chosen would depend on the needs of patient 18. For instance, where patient 18 was highly dependent on the therapy provided by implantable medical device 16, patient 18 may find it desirable to seek to ensure that rechargeable power source 24 not go below a relatively high percentage of total charge. Likewise, where patient 18 knows that access to external charging device 48 may become limited on short notice, such as where patient 18 is frequently compelled to be away from home for extended periods on short notice, it may be desirable to maintain rechargeable power source 24 at a high level of charge. By contrast, a patient 18 who knows there will be readily available access to external charging device 48, or whose therapy is not so highly critical that a temporary interruption would lead to significant discomfort or death, might avoid the relative inconvenience of having to recharge rechargeable power source 24 frequently in favor of allowing rechargeable power source 24 to discharge to a greater extent and thus recharge less frequently.

It is envisioned that reminders for recharging may be delivered to a patient based on a variety of different factors. In one alternative, a user may be allowed to enter a particular percentage level of charge at which the reminder is to be delivered. Alternatively, reminders may be delivered based not on the charge in rechargeable power source 24, but rather based on time elapsed since a previous recharging session, or based on a particular date or time.

Figure 5:
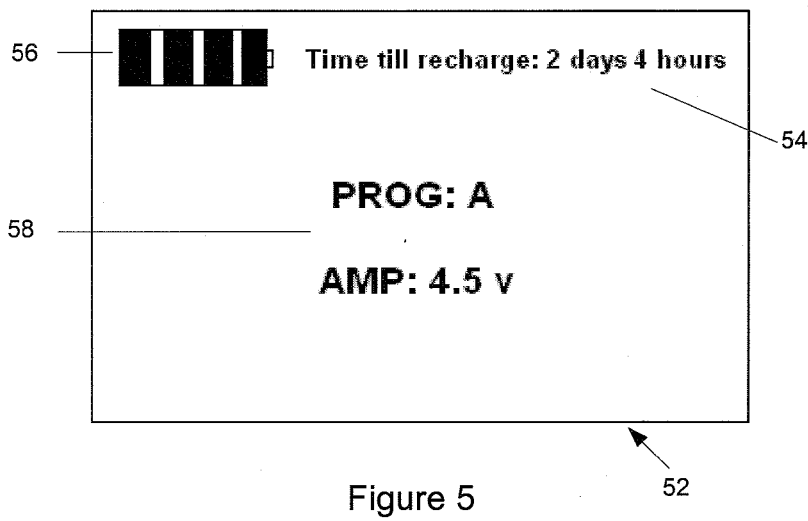
FIG. 5 shows a screen shot of a window for displaying an estimate of the time it will take to recharge an implantable medical device.

FIG. 5 shows a screenshot 152 that displays to a user the anticipated time 154 until recharge will be recommended. Included is a graphical representation 156 of the amount of charge left in rechargeable power source 24. In addition, information 158 pertaining to the operating parameters of implantable medical device 16 is displayed. In an embodiment, this information includes the pre-set program at which implantable medical device 16 is operating, and the voltage being delivered by rechargeable power source 24, though the display of other information is contemplated.

Figure 6:
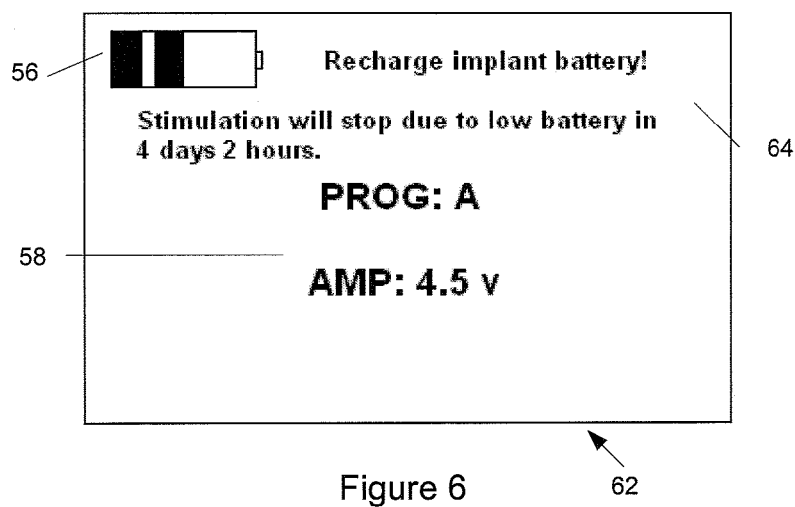
FIG. 6 shows a screen shot of a window for displaying a warning that the rechargeable power source of an implantable medical device is running low and an estimate of time before cessation of therapy is required if the implantable medical device is not recharged.

FIG. 6 shows a screenshot 162 that warns a user that the time has come to recharge rechargeable power source 24. Warnings 164 inform the user that rechargeable power source 24 needs to be recharged, and gives an estimate as to how much time remains before implantable medical device 16 will need to cease delivering therapy in order to conserve power. Graphical representation 156 shows approximately the amount of charge remaining in rechargeable power source 24; in this example, because the battery is depleted graphical representation 156 indicates less than full charge. Information 158 pertaining to the operating parameters of implantable medical device 16 is also displayed.

Figure 7:
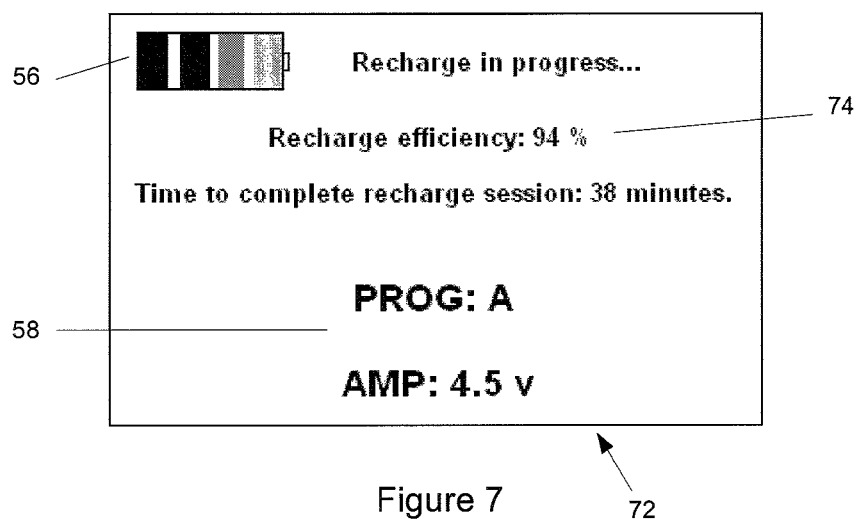
FIG. 7 shows a screen shot of a window for displaying information relating to a recharging session in progress.

FIG. 7 shows a screenshot 172 that provides a user with information relating to a recharging of rechargeable power source 24 while the recharging is in process. Information 174 pertaining to the recharging is displayed, including the efficiency of the connection between primary coil 54 and secondary coil 34, and the estimated time needed to complete the recharging. Graphical representation 156 indicates both that the charge in rechargeable power source 24 is less than full, due to the black bars not fully filling the outline of the battery, and that rechargeable power source is receiving charge by depicting some bars as shaded, rather than either black or white. Information 158 pertaining to the operating parameters of implantable medical device 16 is also displayed.

Figure 8:
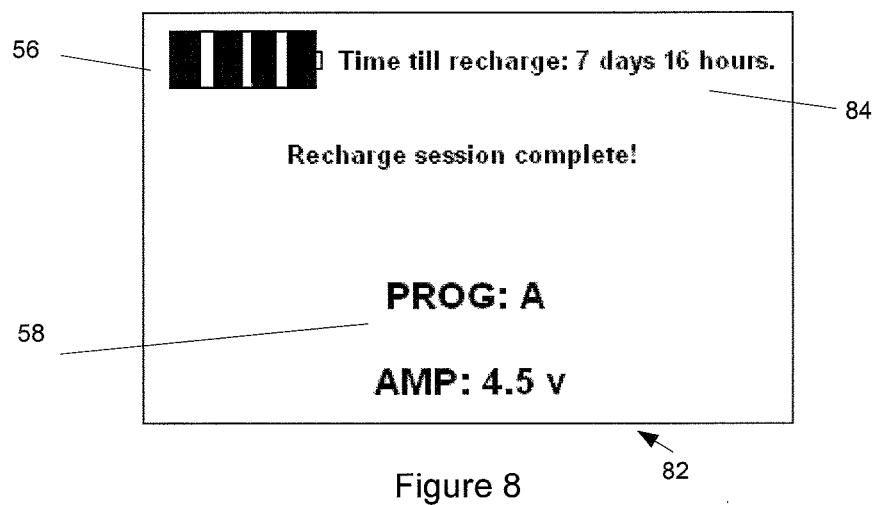
FIG. 8 shows a screen shot of a window for displaying information relating to expected time until recharge will again be required after a recharge has been completed.

FIG. 8 depicts a screenshot 182 that provides a user with information after a recharge session is complete. Information 184 pertaining to the completed recharging is displayed, including informing the user that the session is complete, as well as an estimate of the amount of time before the next recharging of rechargeable power source 24 should occur. Graphical representation 156 indicates that the charging is complete by displaying a full battery symbol, while information 158 pertaining to the operating parameters of implantable medical device 16 is also displayed.

Figure 9:
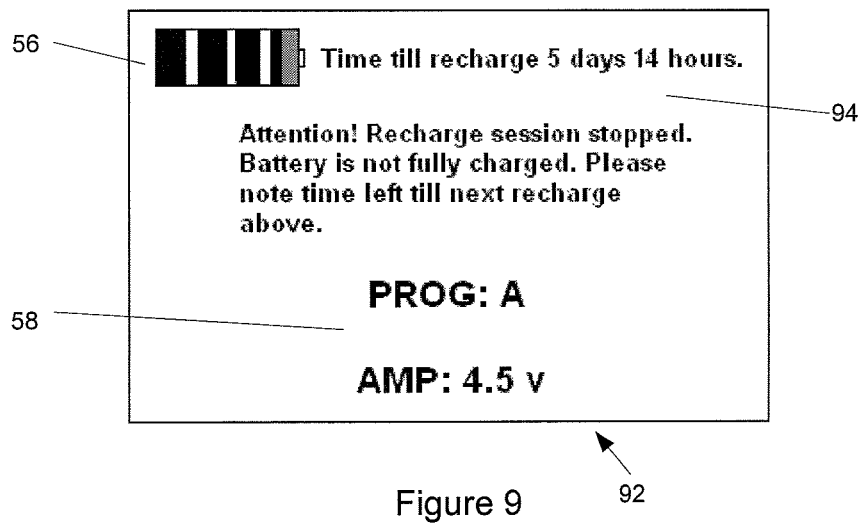
FIG. 9 shows a screen shot of a window for displaying information relating to expected time until recharge will again be required after a recharge session has been aborted before completion.

FIG. 9 shows a screenshot 192 that provides a user with information if the user cancels or aborts a recharge session before the recharge session has completed. In an alternative embodiment, screenshot 192 is displayed if a user indicates an intention to abort or cancel a recharge session before the recharge session is complete. Information 194 informs the user that the recharge session has been stopped before rechargeable power source 24 has been completely charged, and informs the user as to the estimated time before another recharge session should be commenced. Graphical representation 156 indicates that rechargeable power source 24 is not yet fully charged, while information 158 pertaining to the operating parameters of implantable medical device 16 is also displayed. It is to be recognized and understood that the above described information could also be displayed outside of charging session.

It is also possible to determine any and/or all of the required parameters, e.g., charge level of the rechargeable power source and the amount of therapy being delivered, for determining the time until next recharge by telemetry from the implantable medical device while the recharge session is in process and then estimate the time until next recharge session is needed.

While the screenshots of FIGS. 4-9 have been illustrated as liquid crystal displays, it is to be recognized and understood that other forms of display, e.g., LED, CRT, or communication, e.g., aural sounds or synthesized speech, may be utilized either instead of the displays illustrated or in addition thereto.

Figure 10:
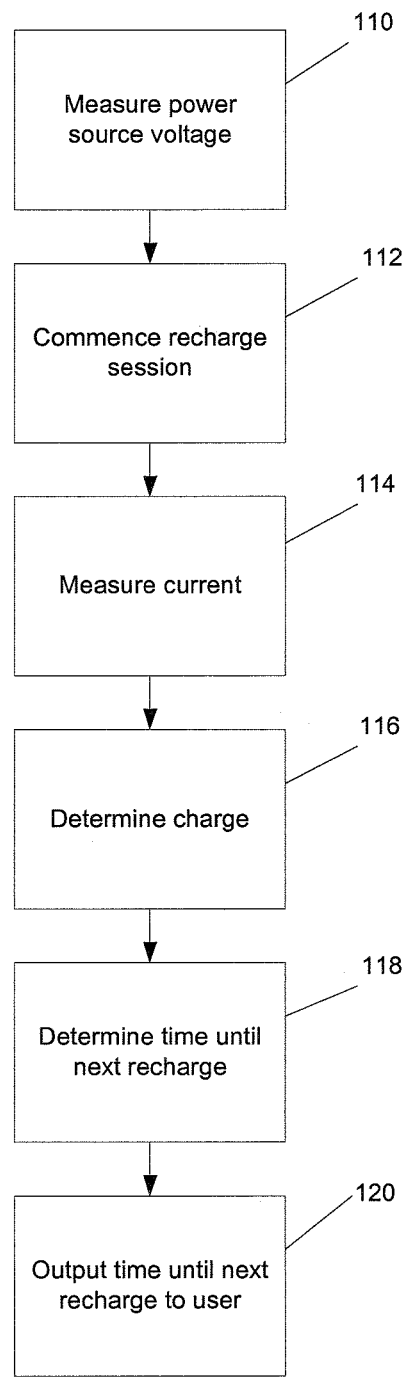
FIG. 10 shows a flow chart for conducting a time until recharge measurement during a recharge session without suspending charging.

In an embodiment, a user may obtain an estimate of the time until recharge if the recharge session is still in progress and while charge is being delivered to rechargeable power source (FIG. 10) using electronic componentry such as electronics 51. When a user uses an external device such as external charging device 48 to initiate a recharge session, implantable medical device 16 measures (110) the voltage across rechargeable power source 24, and stores the value in implantable medical device 16 or in external charging device 48, or, in alternative embodiments, in storage operatively coupled to implantable medical device 16 or external charging device 48. Charging of rechargeable power source 24 then commences (112), with implantable medical device 16 measuring (114) the amount of current that is passing into rechargeable power source 24. This may be accomplished using an ammeter, or by measuring the input voltage to rechargeable power source 24 and computing current based on that input voltage and a pre-measured resistance over the rechargeable power source.

When implantable medical device 16 outputs the measured current value to external charging device 48, either periodically, aperiodically or upon request, external charging device may apply the measured current value and the measured starting voltage value to an experimentally derived model unique to each type of rechargeable power source 24, which may determine (116) the amount of charge in rechargeable power source 24. In an embodiment, the experimentally derived model may be derived in pre-production testing of a plurality of batteries, wherein measured starting voltage levels and charging current data from each battery is recorded, and then, when charging is either completed or suspended, the measured values may be compared against the charge values measured once charging has been suspended. In an embodiment, charging is suspended immediately after each charging current measurement, and the charge on the battery is then measured, and the relationship between the starting voltage and the charging current against the measured charge is recorded. A model based on voltage may be determined in a similar manner, with voltage measurements being followed immediately by a cessation of charging and a second voltage measurement to determine the relationship between a voltage measurement during charging and a voltage measurement without charging with the battery at the same or very nearly the same actual charge. Determining a model applicable to most batteries of a given type may require testing tens or hundreds of the batteries of the type, and may require tens or hundreds of measurements for each battery.

Figure 11:
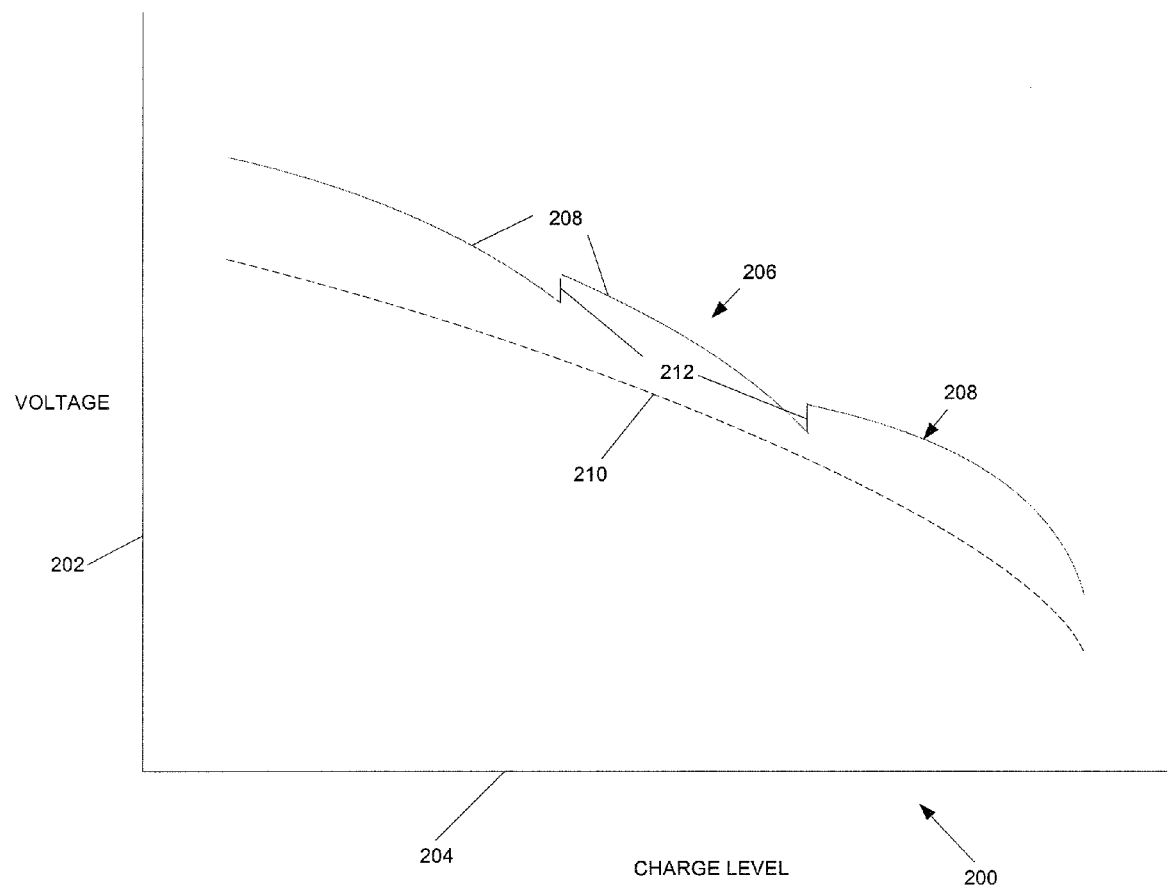
FIG. 11 shows a graphical representation of a model for estimating charge in a rechargeable power source during charging based on voltage.

FIG. 11 shows a graphical representation of a model 200 based on voltage derived from testing one or more batteries in the manner described above. The graphical representation depicts charge level 204 in rechargeable power source 24 as a function of measured voltage 202 over rechargeable power source 24. For various measured voltage values referenced to voltage curve 206, a value of actual battery voltage 210 and charge level 204 may be determined by dropping a line perpendicular to the X-axis of the graph from voltage curve 206 and charge level 204. In an embodiment, voltage curve 206 may comprise two or more distinct intervals 208 which arise from characteristics of rechargeable power source 24 that make it potentially harmful to rechargeable power source 24 to input the same input voltage over the entire recharging of rechargeable power source 24. Instead, as rechargeable power source 24 nears full charge the input voltage may be reduced, thereby resulting in abrupt transitions 212 to the voltage curve 206. It may be seen in the illustrated embodiment that when the measured voltage applied on voltage curve 206 is relatively high, the charge level is relatively low, reflecting that relatively higher measured voltage values reflect a rechargeable power source 24 with a relatively low charge. Where a measured voltage value corresponds to voltage curve 206 around transitions 212, model 200 may need to account for the fact that the same voltage value may result in different determined charge levels 204. Such an accounting may be made by tracking in which distinct interval 208 charging is presently occurring, or by simply allowing for somewhat greater uncertainty in model 200 around transitions 212.

Figure 12:
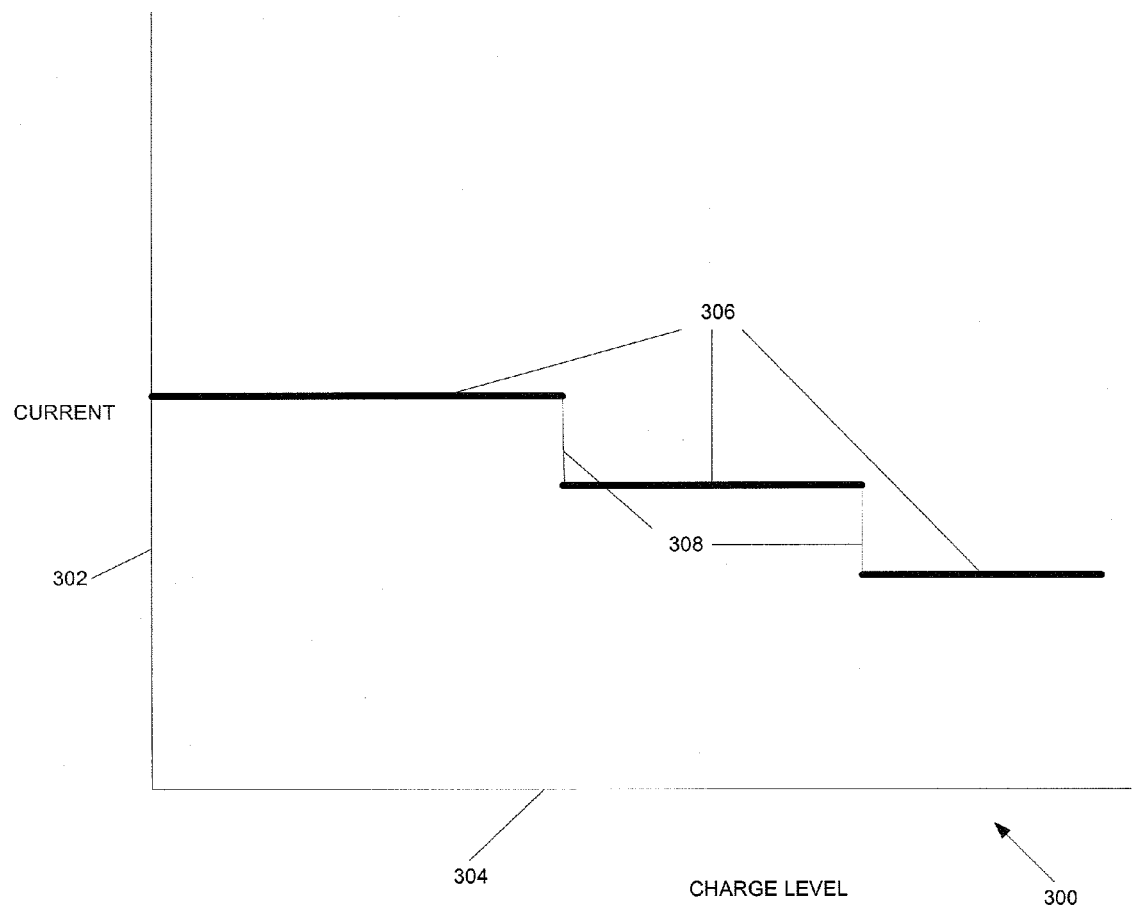
FIG. 12 shows a graphical representation of a model for estimating charge in a rechargeable power source during charging based on current.

FIG. 12 shows a graphical representation of a model 300 based on current derived from testing one or more batteries in the manner described above. The graphical representation reflects charge level 304 in rechargeable power source 24 as a function of input current 302 into rechargeable power source 24. In an embodiment, input current 302 may be determined by a coulomb counter placed in series with the input to rechargeable power source that measures the coulombs that transfer into rechargeable power source 24; in such an embodiment, input current 302 may be relabeled input charge 302, but, as will be shown, model 300 functions fundamentally the same, regardless of whether charge or current is measured. In one embodiment, the input current 302 or input charge 302 may be measured over the entire course of a recharge. If coulombs are measured, that will reflect the actual amount of charge transferred to rechargeable power source 24. If current is measured, the integral of input current 302 over the entire recharge time will yield the number of milliamp hours. In either event, because of the relationship that one coulomb equals approximately 0.00027778 amp-hours, the charge input to rechargeable power source 24 may be determined. Note that because of the desirability of reducing the input voltage into rechargeable power source 24 as rechargeable power source 24 nears full charge, as described above, there may be transitions 308 in input current or input charge 306. However, unlike with respect to voltage, such transitions 308 may not create uncertainty or have to be accounted for when model 300 relates to charge or current.

In an alternative embodiment, current or charge is not measured over the entire recharge procedure, but rather over a relatively brief time interval. Then, based on input current curve 306 or input charge curve 306 and the length of time the recharge procedure has been occurring and where on curve 306 the recharge procedure started, it may be approximated where on curve 306 the recharge procedure presently is, which may give an estimated time until recharge. In an embodiment, a user may select a desired time interval over which the measurement takes place. In various embodiments, an increased measurement time results in a decreased impact of small fluctuations of input current or input charge on the estimated charge level in rechargeable power source 24. However, because the current meter or coulomb counter is in series with the input to rechargeable power source 24, utilizing the current meter or coulomb counter may reduce the input current into rechargeable power source 24 due to the inherent increase in input resistance realized by the addition of additional series components. Thus, the shorter the time interval, the faster the recharging may progress. A user may weigh on a case-by-case basis the benefits of relatively more accurate estimates of charge in rechargeable power source 24 against the benefits of reduced recharge time.

In an embodiment, a model may utilize both voltage and current or charge, as illustrated in model 200 and model 300. A model that utilizes both models 200 and 300 may utilize one model, such as model 300, to establish an estimated time until recharge, and then utilize the other model, such as model 200, to develop a second estimate to verify the accuracy of the first estimate. Alternatively, the two estimated times until recharge may be averaged to create an estimated time until recharge that is outputted to a user. Alternatively, the two estimated times until recharge may be weighted.

Returning to FIG. 10, external charging device 48 may then determine (118) the amount of time the charge in rechargeable power source 48 may last until the user would have to recharge rechargeable power source 24 once again. This determination may based on the factors including: amount of charge currently in rechargeable power source 24, the projected consumption of charge by implantable medical device 16, and the level at which the user would be prompted that their implantable medical device 16 needs to be recharged, based at least in part on the response given by the user (see FIG. 4). The projected consumption of charge determination may be based on the present settings of implantable medical device 16, particularly relating to the delivery of therapy, but also relating to non-therapy related settings that influence power consumption, such as the amount of time electronics 26 may be expected to be in active operation. In addition to these factors, any history that might be stored relating to patient 18 behavior and activities that could impact power consumption may also be used, such as patient initiated therapy and various anticipated patient activities, such as exercise or sleep. As an example, stipulate that rechargeable power source 24 is determined to presently have 100 kilo-coulombs of charge, and, based on the settings of implantable medical device 16, and the further device history that says that patient 18 is unlikely to alter the settings, that, based on the programmed rate of therapy delivery, the device is expected to consume approximately 10 kilo-coulombs per 24 hour period. Further stipulate that implantable medical device 16 is programmed to indicate recharging when 10 kilo-coulombs remain in rechargeable power source 24. In this case, rechargeable power source 24 may be expected to discharge down to the level wherein recharging is indicated in (100−10)/(10/24)=216 hours, which would constitute the determined time. External charging unit 48 may then output (120) the determined time to the user.

In an alternative embodiment, a time until recharge may be determined in the same manner described above, but for a prospective therapeutic output instead of a present therapeutic output as illustrated above. In such an embodiment, where a user utilizes a user input (in an embodiment, a user input adapted from the user input depicted in FIG. 4) to set a prospective therapeutic output, the prospective rate of the prospective therapeutic output is utilized in the above equation to determine the amount of time until recharge if the prospective therapeutic output were implemented. Thus, a user would be able to know in advance of actually programming implantable medical device 16 with a new therapy regimen what impact the new regimen would have on the charge life of rechargeable power source 24.

It is envisioned, in various embodiments, that the above described calculations may be conducted in electronic componentry residing in one or more of various possible locations. In an embodiment, the calculations may be conducted in electronic componentry located in electronics 51 in external charging unit 48. In an alternative embodiment, the calculations may be conducted by electronic componentry located in, or which is a part of, electronics 26 of implantable medical device 16. In further embodiments, the calculations may occur in electronic componentry located in other devices that are configured to operatively couple with implantable medical device 16 or external charging unit 48, such as a patient programmer or a physician programmer, or any other suitable device with electronics that may perform such calculations and, optionally, which includes an interface for operatively coupling between the device and external charging unit 48 or implantable medical device 16.

Figure 13:
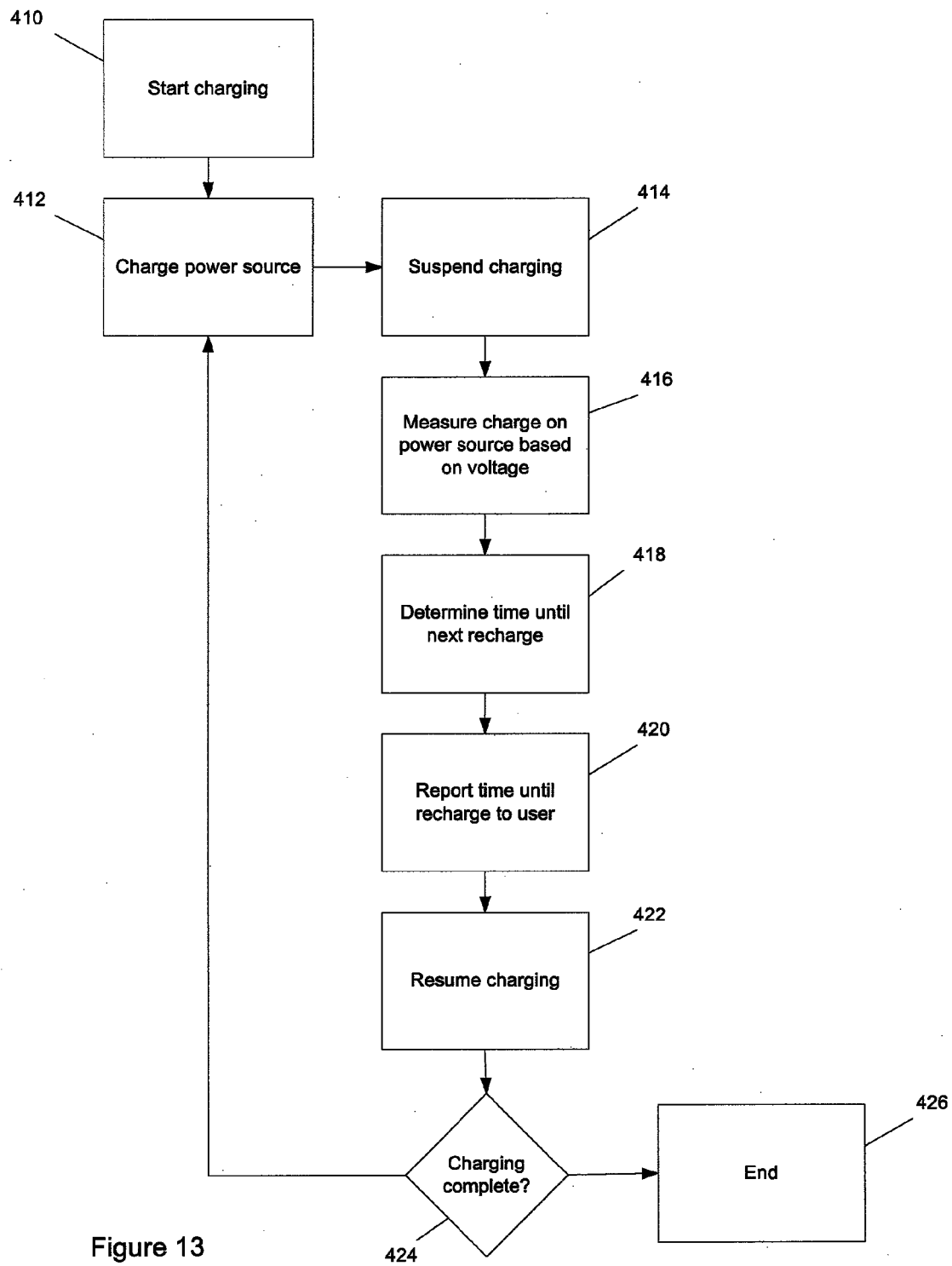
FIG. 13 shows a flow chart for conducting a time until recharge measurement during a recharge session while suspending charging.

In an alternative embodiment (FIG. 13) the charging of rechargeable power source 24 may be temporarily suspended during the recharging session while measurements are taken to determine the level of charge currently in rechargeable power source 24. In an embodiment, the user begins the recharge session via external charging device 48, and the recharge session for charging rechargeable power source begins (410). Charge is supplied (412) to rechargeable power source in a manner such as has been described above, until charging is suspended (414). The voltage from rechargeable power source 24 may then be measured (416) and used to determine the charge in rechargeable power source by demonstrating the percentage of the charge capacity of rechargeable power source 24 that is currently filled with charge. It is known in the art that rechargeable power supply 24 types may be characterized by measuring the voltage at various times during the discharging of individual ones of the type, and that the percentage of the total charge remaining in rechargeable power supply 24 may remain the same for each measured voltage value. Thus, by testing enough rechargeable power sources 24 of each type at enough voltage levels, the rechargeable power source 24 type may be characterized such that, for any given measured voltage, the percent charge remaining may be determined based on the past results, and from the percent remaining, the total charge may be determined.

Based on the measured charge, external charging device 48 may determine (418) the time until recharge in the same manner described above (see FIG. 10, (118)), and the time is reported (420) to the user. In various embodiments, the time may be reported on patient programmer, or on any external device configured to communicate with implantable medical device 16 and which is associated with a display. Charging of rechargeable power source may then be resumed (422), and a determination may be made whether charging is complete (424). If not, charging may continue (412). If so, the recharging session may terminate (426).

Thus, embodiments of the time to next recharge session feedback while recharging an implantable medical device, system and method therefore are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A recharge management system for use during a recharging session, comprising;
an implantable medical device having a rechargeable power source;
an external charger configured to charge said rechargeable power source when placed in proximity to said implantable medical device;
electronic componentry, operatively coupled to said implantable medical device, configured to determine a recharge interval from a present time until a time for next recharge should said recharging session not continue, said recharge interval being an interval until a recharge time when a charge level of a rechargeable power source of said implantable medical device reaches a value at which recharging of said rechargeable power source is indicated; and a user output, operatively coupled to said electronic componentry, configured to communicate said recharge interval to a user.

2. The system as in claim 1 wherein said electronic componentry determines said recharge interval by applying a model.

3. The system as in claim 2 wherein said electronic componentry is further configured to measure an initial power source voltage of said rechargeable power source before said external charger begins to charge said rechargeable power source, and wherein said implantable medical device further comprises a current meter, said current meter configured to measure current to said rechargeable power source, and wherein said model utilizes said initial power source voltage and said measured current to determine said recharge interval.

4. The system as in claim 1 wherein said rechargeable power source has a power source voltage, a charge capacity and a charge level, and wherein said electronic componentry is further configured to:
measure said power source voltage during a time in which said external charger has suspended charging of said rechargeable power source;
determine said charge level as a function of said power source voltage and said charge capacity; and
determine said recharge interval based on said charge level.

5. The system as in claim 1 wherein said recharge interval is determined based on a present programmed rate.

6. The system as in claim 1 wherein said recharge interval is determined based on a past programmed rate.

7. The system as in claim 1 wherein said recharge interval is determined based on a present programmed rate and a past programmed rate.

8. The system as in claim 7 wherein said implantable medical device has a programmed therapeutic output having a programmed rate, and wherein said recharge interval is further determined based on said programmed rate.

9. The system as in claim 8 further comprising a user input, wherein said user inputs via said user input a prospective therapeutic output having a prospective rate, and wherein said recharge interval is determined based on said prospective rate should said recharging session not continue.

10. The system as in claim 1 further comprising a user input wherein said user inputs a desired time interval, wherein said rechargeable power source further comprises a present charge level, and wherein said electronic componentry further determines an estimated time to charge said rechargeable power source based on said present charge level and said desired time interval.

11. The system as in claim 10 wherein said user input is a component of said external charger.

12. The system as in claim 1 wherein said electronic componentry is a component of said implantable medical device.

13. The system as in claim 1 wherein said electronic componentry is a component of said external charger.

14. The system as in claim 1 wherein said user output is a component of said external charger.

15. A device implemented method for determining a recharge interval, said recharge interval being an interval from a present time until a recharge time when a charge level of a rechargeable power source of an implantable medical device reaches a value at which recharging of said rechargeable power source is indicated, comprising the steps of:
charging said rechargeable power source with an external charger during a recharging session;
determining, during said recharging session, said recharge interval should said recharging session not continue; and
outputting said recharge interval to a user.

16. The method as in claim 15 wherein said determining step determines said recharge interval by using a model.

17. The method as in claim 16 further comprising the step of measuring an initial power source voltage of said rechargeable power source before said charging step begins, and wherein said charging step further comprises measuring a measured current to said rechargeable power source, and wherein said model utilizes said initial power source voltage and said measured current to determine said recharge interval.

18. The method as in claim 15 wherein said rechargeable power source has a power source voltage, a charge capacity and a charge level, and wherein said determining step further comprises:
suspending said charging step;
measuring said power source voltage;
recommencing said charging step,
determining said charge level as a function of said power source voltage and said charge capacity; and
determining said recharge interval based on said charge level.

19. The method as in claim 15 wherein said recharge interval is determined based on a present programmed rate.

20. The method as in claim 15 wherein said recharge interval is determined based on a past programmed rate.

21. The method as in claim 15 wherein said recharge interval is determined based on a present programmed rate and a past programmed rate.

22. The method as in claim 21 wherein said implantable medical device has a programmed therapeutic output having a programmed rate, and wherein said recharge interval is further determined based on said programmed rate.

23. The method as in claim 22 further comprising the step of selecting, by said user, a prospective therapeutic output having a prospective rate, and wherein said determining step determines said recharge interval based on said prospective rate should said recharging session not continue.

24. The method as in claim 15 wherein said rechargeable power source further comprises a present charge level, further comprising the step of inputting, by said user, a desired time interval, and further comprising the step of determining an estimated time to charge said rechargeable power source based on said present charge level and said desired time interval.

* * * * *